United States Patent [19]

Hochstrasser

[11] 3,964,871
[45] June 22, 1976

[54] METHOD AND DEVICE FOR DETECTING GLUCOSE

[75] Inventor: Harry Hochstrasser, Hastings-on-Hudson, N.Y.

[73] Assignee: Becton, Dickinson and Company, East Rutherford, N.J.

[22] Filed: Dec. 18, 1974

[21] Appl. No.: 533,972

[52] U.S. Cl. .......................... 23/253 TP; 23/230 B; 116/114 AM; 195/103.5 C; 195/127
[51] Int. Cl.² ........................................ G01N 33/16
[58] Field of Search .................. 23/230 B, 253 TP; 195/103.5 R, 127, 103.5 C; 116/114 AM

[56] References Cited
UNITED STATES PATENTS

| | | | |
|---|---|---|---|
| 2,464,155 | 3/1949 | Russell et al. | 23/253 TP |
| 2,799,167 | 7/1957 | Loconti | 23/253 TP |
| 3,006,735 | 10/1961 | Jordan | 23/253 TP |
| 3,036,894 | 5/1962 | Forestiere | 23/253 TP |
| 3,050,373 | 8/1962 | Collins | 23/253 |
| 3,139,328 | 6/1964 | Jacob | 23/253 TP |
| 3,235,337 | 2/1966 | Artis | 23/253 TP |
| 3,290,228 | 12/1966 | Gretton et al. | 195/127 |
| 3,350,278 | 10/1967 | Gretton et al. | 195/127 |
| 3,411,887 | 11/1968 | Ky | 23/230 B |
| 3,453,180 | 7/1969 | Fraser, Jr. et al. | 23/230 B |
| 3,667,916 | 6/1972 | Sliva et al. | 23/253 TP |
| 3,699,003 | 10/1972 | Kronish et al. | 23/253 TP |
| 3,810,739 | 5/1974 | Nussbaum | 23/253 TP |
| 3,814,668 | 6/1974 | Blake et al. | 195/103.5 C |

*Primary Examiner*—R.E. Serwin
*Attorney, Agent, or Firm*—Kane, Dalsimer, Kane, Sullivan and Kurucz

[57] ABSTRACT

A disposable indicator is disclosed which is useful for the measurement of substances, e.g., glucose, in biological fluids. The instrument registers the concentration of substance in a given biological fluid with indicia which are directly readable in a convenient notation system (e.g., digital or other symbolic notation). The indicator comprises an improvement over prior art disposable devices which require a comparison of the viewable indication with a color intensity scale to translate the indicia registered to meaningful numerical values or other symbolic notations. The indicator permits the use of chemical reagent concentrations which are at least an order of magnitude greater than those used in prior art, thereby improving stability and drastically lowering the magnitude of interferences. As an example, the use of the indicator of the invention in conjunction with novel reagent compositions in the determination of urinary glucose concentrations is disclosed.

21 Claims, 10 Drawing Figures

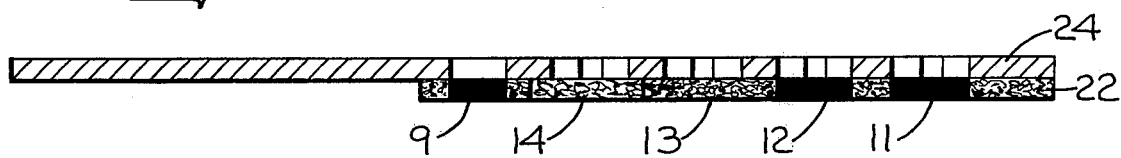
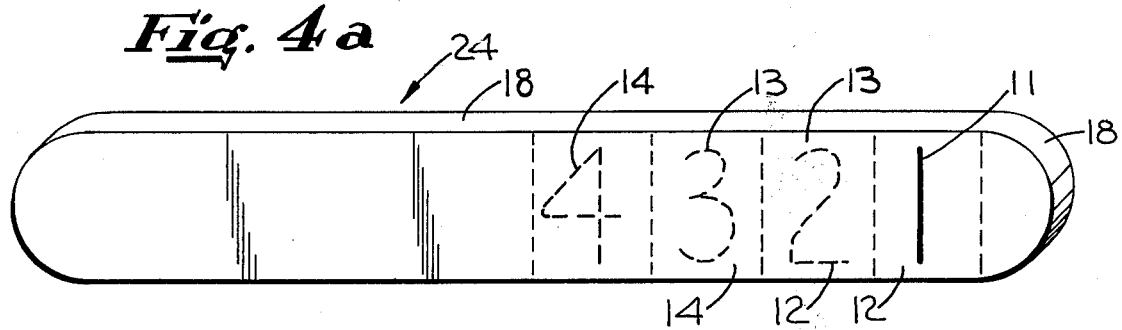
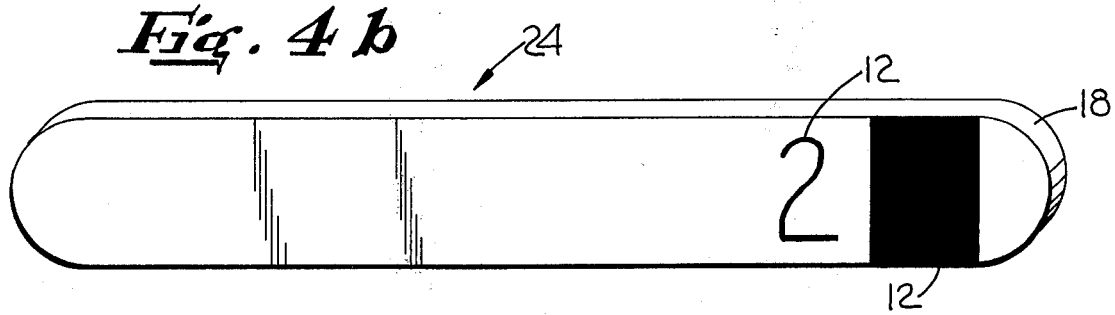
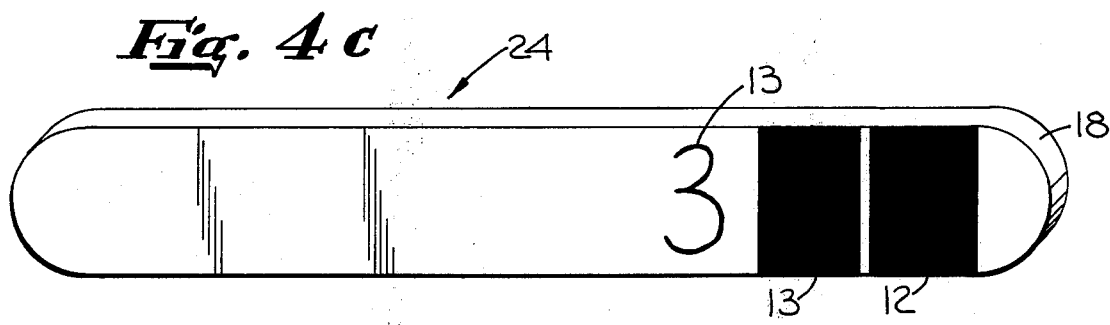
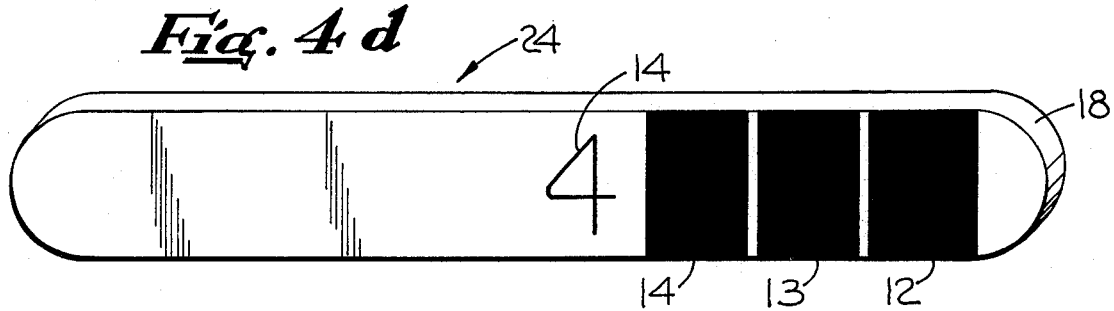

METHOD AND DEVICE FOR DETECTING GLUCOSE

BACKGROUND OF THE INVENTION

1. Field of the Invention

The invention concerns devices for the quantitative analysis of chemical substance concentrations in biological fluids and more particularly concerns a disposable device useful for determining the glucose content of biological fluids. The invention also concerns methods of making and using the devices of the invention.

2. Brief Description of the Prior Art

Prior hereto, disposable devices have been known and commercially available which are useful for determining the concentration of glucose (and other substances) in liquids. Of particular importance for their simplicity, low cost, ease of operation and widespread use are the relatively simple devices which comprise a strip of bibulous material or other support element bearing a reagent which yields a color indication upon contact with glucose. Representative of such devices are the devices described in U.S. Pat. Nos. 2,865,718; 2,848,308; 2,893,844; 2,981,606; 3,164,534; 3,212,855; and 3,791,988.

The devices described in the above prior art patents all operate by immersion in e.g. a glucose containing solution for brief periods of time. On contact with glucose, the reagent element of the device undergoes a chemical change, which is indicated visually to the operator by a color change. Generally, the degree of color change is a crude measure of the concentration of glucose in the immersion liquid. For example, the device of U.S. Pat. No. 2,981,606 employs a reagent composition which gives a color indication, depending on the concentration of glucose in the immersion liquid, varying from tints of yellow to green to blue. An approximation of the glucose content of the immersion solution in terms of percentage is then obtained by comparing the color indication with color shades obtained by exposure of the reagent to solutions of known glucose content. In practice, a secondary color comparison chart is used.

Other devices of the prior art employ a single reagent which is sensitive to glucose above a specific concentration. These latter devices, as represented by the devices disclosed in U.S. Pat. No. 2,893,844, also give the operator a visual indication by color formed upon reaction of the reagent element with glucose. The devices do not indicate a range of concentrations, but only indicate if a certain predetermined level of glucose is present or exceeded in the solution being tested.

The disposable devices of the prior art have not offered a means of obtaining a direct numerical reading of glucose or other substance content of the tested solutions. For this determination, either a comparison with a color chart must be made to convert the indicia registered by the device to a numerical value or multiple tests would have to be carried out using a separate indicator device for a number of different minimum glucose level determinations. Both devices offer only a crude approximation of glucose concentrations and are dependent upon the ability of the user of the device to differentiate shades of colors.

A further disadvantage of the commercially available prior art devices resides in the fact that they must be employed following closely defined operating rules. More particularly, the reagents employed continue to react after initial contact with the substance to be detected, such as glucose. The colors formed by the reagents continue to develop to the darkest shade possible and so the indicator must be read within a narrow and specific time period following immersion if any accuracy is to be obtained in the determination. If the operator fails to understand the criticality involved in reading the indicia registered within the prescribed time, or fails to do so accurately, an erroneous reading will be obtained. The indicators of my invention are disposable, register an indicia of dissolved substance concentration which is directly readable in numerical terms and will indicate over any desired range of possible concentrations. In addition, the indicators of my invention provide a registration soon after brief immersion in the containing solution and do not have to be "read" within a critical time period following such immersion. The indicia registrations obtained are stable for reasonably long periods following exposure (particularly to glucose) so that a degree of freedom is obtained as to when the registration must be observed for an accurate reading.

Furthermore, instruments of my making, prepared according to the invention are comparatively insensitive to the effects of interfering substances in the test specimens. In the case of prior art glucose determinations in urine for example, the presence of certain reducing substances such as 2,5-dihydroxy benzoic acid or ascorbic acid in the urine masks the presence of glucose; see for example Feldman et al., Diabetes, Vol. 19, No. 5, Pps. 337–343.

This leads to the creation of potential gross errors in diagnosis and to the erroneous administration or withholding of certain therapeutic drugs. In using the instruments and reagent formulation of my invention however, the effects of such interferences are virtually eliminated, i.e. reduced to about 3% of the effect seen with prior art instruments.

Enzyme based reagent compositions for the determination of glucose in glucose containing solutions known prior to my invention are represented by U.S. Pat. Nos. 2,848,308; 2,981,606; 3,164,534; 3,721,607; and 3,791,988; and the article "Morin et al, Clinical Chemistry, 10/9, 959–952 (1973)"; plus others too numerous to list. Although many of such compositions may be employed in fabricating the indicators of my invention, the preferred indicators employ glucose sensitive reagents which comprise novel compositions of the invention. The novel compositions of the invention, hereinafter described more fully, are advantageously used in the fabrication of the indicators of the invention. The novel compositions are particularly advantageous reagents for the quantitative determination of glucose, being rapid acting and of anticipated enhanced storage stability and result in a reduction of the magnitude of the effect due to interfering substances to about 3% of the effect seen in the use of prior art devices and compositions when used in an instrument of the invention as discussed above. Although the ratio of equivalent proportions of reducing or antagonist compound to equivalent proportion of glucose to be detected may vary within a range of from about 1:1 to 5:1, it is preferred that the ratio be substantially stoichiometric. By stoichiometric I means those amounts which are substantially in the same proportion as the chemically equivalent weight for the reacting species. When my compositions are used, this ratio is essentially stoichiometric, i.e. and therefore predictable and easily controlled in manufacture. Furthermore, only when my preferred compositions are used do I observe the relative absence of interference from reducing substances that may occur in urine and which mask large amounts of glucose, in the case of prior art devices (see above).

SUMMARY OF THE INVENTION

The invention comprises an indicator for the measurement of substances dissolved in biological fluids, which comprises; a support member; and a plurality of indicating reagents for said substances, each of which is located in a separate zone of said member and at least two of which indicate the presence of a different concentration of said substance in solution, by causing the registration of convenient symbols, including digits.

The invention also comprises a method of making the devices of the invention.

The invention also comprises a method of determining the concentration of a chemical compound in a solution, which comprises; immersing an instrument of the invention in the compound containing solution, removing said instrument from said solution and reading the indicated concentration of the chemical substance directly from the instrument. The method is particularly advantageous for determining the concentration of glucose in a solution.

The invention also comprises novel glucose indicating compositions which comprise; glucose oxidase; horseradish peroxidase; a compound which forms a color upon oxidation by hydrogen peroxide in the presence of horseradish peroxidase; an antagonist compound selected from indoxyl sulfate; uric acid; 3,4-dihydroxymandelic acid; 3-methoxy-4-hydroxymandelic acid; 3,4-dihydroxyphenylacetic acid; 3-methoxy-4-hydroxyphenylacetic acid; 3,4-dihydroxyphenylalanine; 3-methoxy-4-hydroxyphenylalanine; 5-hydroxyindole-3-acetic acid; 5-hydroxyindole-2-carboxylic acid; 5-hydroxytryptophane; creatinine; 2,5-dihydroxyphenylacetic acid; o-hydroxytyramine (dopamine); 5-hydroxytryptamine; and 2,5-dihydroxybenzoic acid; and a buffer composition which will maintain the pH of said glucose indicating composition within the range of from about 4 to about 6 in the presence of biological fluids such as blood, urine, tears, saliva and the like.

The term "antagonist compound" as used throughout the specification and claims means a compound which will prevent in some manner the accumulation of oxidized indicator until such time as said compound has been completely consumed in such reaction. Preferred as the antagonist compound is 2,5-dihydroxybenzoic acid. For convenience, the term "2,5-DHBA" will sometimes be used hereinafter to mean 2 5-dihydroxybenzoic acid.

The compositions of the invention are useful in fabricating the instruments of the invention.

BRIEF DESCRIPTION OF THE DRAWINGS

FIGS. 4a, 4b, 4c and 4d are isometric views of an alternate indicator embodiment of the invention showing the possible indicia registrations after immersion in various glucose containing solutions.

FIG. 6 is a cross-section longitudinal view along lines 6—6 of FIG. 5.

DETAILED DESCRIPTION OF THE INVENTION

Figure 1:
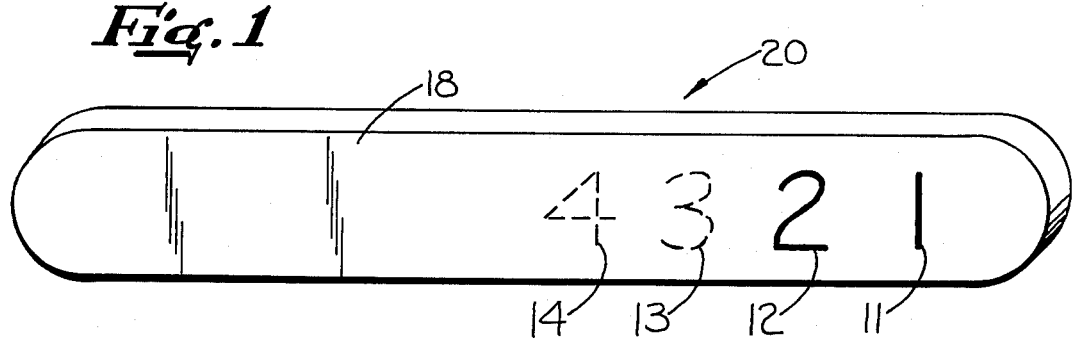
FIG. 1 is an isometric view of an indicator embodiment of the invention, following use in a solution containing glucose.

The indicators of the invention are relatively simple devices which may be used once and thereafter disposed of. For this reason they may be termed "disposable" instruments. Although their most important use may be for the determination of glucose levels in the urine and blood of mammals, they are not restricted to this use and may be employed to determine the presence and concentration of any substance in any biological fluid. For example, by the selection of appropriate reagents, the indicator devices of the invention may be employed to determine the concentration of ketones, albumin, nitrogen, etc. in urine or urea, calcium, protein, albumin, chloesterol, triglycerides, alkaline phosphatase, bilirubin, uric acid, etc. in blood plasma or blood serum.

The indicators of the invention comprise a support member bearing a plurality of specific reagents. The support member is not critical in the sense that a specific material of construction is required although several forms of preferred embodiments will be described hereinafter. In general, the support member may be of any material capable of bearing the reagent for exposure to the solution to be tested. Specific examples of support members are webs, sticks, strips, splinters, sheets, rods and like forms of glass, metal, wood, paper; polymerics such as polyethylene, polypropylene, polyalkylene acetate, polycarbonates and the like; textiles and the like. Preferred materials are the bibulous materials which may be impregnated with solutions of reagent compositions, such as filter papers, blotting papers and like bibulous materials.

The reagent components of the indicators of the invention are preferably prepared in a liquid form for deposit upon the support member. Once placed on the support member, the reagent compositions in solution are dried to adhere the compositions to the support member. Generally, adhesion of the reagent compositions to the support member is conveniently effected when the support member is a bibulous material. Conventionally employed inert fillers, binders, surfactants and the like may be incorporated into the reagent compositions when desired. Certain binders such as resin gums are advantageously incorporated into the reagent compositions to assist in adhering them to non-porous support members such as metal, glass or non-porous polymeric materials. For product elegance, it is desirable that the color change in each indicator zone of the devices of the invention be clear, sharp, unequivocal and strongly positive. I have found that the degree of accuracy and precision with which the devices of the invention function in accord with this desire is related to the ratio of volume of reagent solution deposited on the support member to volume of test solution absorbed at the reagent site during immersion in the test solution or biological fluid. The most advantageous device of the invention in terms of accuracy and precision obtainable are those wherein the above described ratio is substantially a 1:1 ratio. The further one departs from this optimum ratio, the greater will be the loss of accuracy and precision in the indicator devices.

To obtain the above-described preferred ratio, it is necessary that a given zone of the preferred bibulous support member be fully saturated with the reagent in a solvent. The solvent is then evaporated to prepare an indicator device of the invention. Upon immersion in the biological solution being tested, the bibulous material at the side of reagent deposition will then generally take up a volume of the test solution which is equivalent to the volume of solvent evaporated resulting in the desired 1:1 ratio described above. However, unless the area of reagent impregnation is isolated in a manner so as to provide a site of precise and determinable volume, the reagent may be carried beyond the site of original deposition upon immersion in the test solution. This will result in dilution of the reagent in terms of its proportion in the absorbed test solution during the test procedure, and ultimately results in a variation from the desired 1:1 ratio described above. Therefore, preferred devices of the invention wherein the indicator reagent is carried on a bibulous material preferably have the plurality of indicator reagent sites separated from each other by a non-absorbent or hydrophobic material and each site preferably will absorb nearly identical volumes of the solvent employed in depositing reagent and of the biological fluid to be tested. The preferred device may be prepared, for example, by affixing a plurality of the reagent impregnated bibulous support members (each bearing a reagent of different sensitivity to the substance being tested for, as described more fully hereinafter) to a different zone of a hydrophobic support member such as a polymeric resin solid strip like polyethylene, polypropylene, etc. Upon immersion of such a device in the test solution, a precise volume of the test fluid is absorbed at the site of the indicator reagent which is then diluted accurately to substantially the same concentration at which it was deposited in the deposition solvent employed in preparing the indicator reagent site. Illustrative of such preferred indicator devices are those described more fully hereinafter, particularly the embodiment of FIGS. 2 and 3.

The reagent components of the indicators of the invention may be any of the known reagents for the quantitative detection of the substance being analyzed for, and which will give a visual indication when exposed to specific concentrations of such substance in a solution thereof. A plurality of such reagents are placed on the support member, each in a different zone of the member and at least two of said reagents providing an indication of different substance-in-solution concentration levels. Such reagents and the means for their preparation are generally known in the case of gulcose testing. Exemplary of reagents which may be employed for determining glucose levels and their method of preparation are the glucose indicating compositions disclosed in U.S. Pat. No. 2,893,844. In general, such reagents comprise an enzyme having glucose oxidase activity, peroxidase, an indicator which undergoes a color change in the presence of hydrogen peroxide and peroxidase and a compound which prevents in some manner the accumulation of oxidized indicator until such time as said compound has been completely consumed in such reaction. Such a compound, conveniently, may be a reductant sufficiently reactive as to reduce any oxidized indicator formed in the enzymatic conversion described above. Examples of the latter compounds are well known and are illustrated by ascorbic acid and the like. An extensive list of such compounds may be found in U.S. Pat. No. 2,893,844.

An alternative method of achieving the same effect is described in "Screening Method for Glucose of Blood Serum Utilizing Glucose Oxidase and an Indophenol Indicator", Leonard Dobrick, *J. Biol. Chem.* 1958, pp. 403–409.

Preferred reagents for use in fabricating the indicators of the invention for use in detecting glucose concentrations are those constituting the above described compositions of the invention. The compositions of the invention are prepared by admixing a glucose oxidase, peroxidase, an antagonist compound, a compound which forms a color upon oxidation by contact with hydrogen peroxide in the presence of the peroxidase, and a buffer composition which will maintain the pH of the reagent composition within the range of from about 4 to about 6 in the presence of biological fluids.

The preferred glucose oxidase employed in preparing the compositions of the invention is a glucose oxidase obtained from molds. Such glucose oxidases are generally well known, see for example U.S. Pat. No. 2,981,606.

Peroxidase is also a generally well known class of enzyme, and any of the known peroxidases such as those described in U.S. Pat. No. 2,981,606 may be employed in preparing the compositions of the invention. Horseradish peroxidase is a preferred peroxidase for preparing the devices of the invention.

Compounds which form a color upon being oxidized by hydrogen peroxide are also generally well known, see for example U.S. Pat. Nos. 2,981,606 and 3,721,607 describing for example color-forming substances which produce a color formation in the presence of hydrogen peroxide and peroxidase. Examples of such compounds which may be employed in the glucose indicators of the present invention include the following substances:

1. Monoamines, such as aniline and its derivatives, ortho-toluidine, para-toluidine, etc.;
2. Diamines, such as ortho-phenylenediamine, N,N'-dimethyl-para-phenylenediamine, N,N'-diethyl phenylenediamine, benzidine (which produces a blue or brown color), dianisidine (turns green or brown), etc.;
3. Phenols, such as phenol per se (producing a yellow color), thymol, ortho-, meta and para-cresols (producing a green-yellow color, a pink color and a milky suspension, respectively), alpha-naphtol (producing a magenta color), beta-naphthol (producing a white precipitate), etc.;
4. Polyphenols, such as catechol, guaiacol (which forms an orange color), orcinol, pyrogallol (producing reddish or yellow color), p,p-dihydroxydiphhenyl and phloroglucinol;
5. Aromatic acids, such as salicylic, pyrocatechuic and gallic acids;
6. Leuco dyes, such as leucomalachite green (to produce malachite green) and leucophenolphthalein (desirably employed in an alkaline medium);
7. Colored dyes, such as 2,6-dichlorophenolindophenol;
8. various biological substances, such as epinephrine, the flavones, tyrosine dihydroxphenylalanine (producing an orange-reddish color) and tryptophane; and 9. Other substances, such as gum quaiac, guaiaconic acid, nadi reagent (producing a bluish color) potassium sodium, and other water soluble iodides; and bilirubin (producing a greenish color).

Buffer compositions which may be employed in preparing the compositions of the invention are generally well known and include for example mixtures of sodium phosphate with sodium phosphate monohydrate and mixtures of citric acid with trisodium citrate.

The components of the compositions of the invention are admixed employing conventional techniques, generally in the presence of a solvent such as water. The order of admixture is not critical, although it is generally preferred to add the antagonist compound component first. The solutions of novel compositions of the invention may then be used to deposit the compositions upon support members to fabricate the indicators of the invention.

Representative preferred compositions of the invention are those prepared using the following proportions of ingredients. About 40 or more IU of glucose oxidase; about 60 or more purpurogallin units of peroxidase; frrom about 0.05 to about 15 mg. of the compound which forms a color upon oxidation and from about 0.01 to about 5.0 mg. of the antagonist compound, all per 100 microliters of reagent. The buffer component is added in sufficient quantity to maintain the reagent composition at a pH within the range of from 4 to 6 in the presence of biological fluids.

The precise level or concentration of glucose in solution which will be "indicated " by a color change occurring during reaction of the reagent compositions of the invention, is determined by the proportion of antagonist compound employed in preparing the compositions of the invention. Indication of a minimum level of glucose occurs when a given proportion of antagonist compound is exhausted in reducing the indicator dye. By varying the proportion of antagonist compound, one may prepare reagent compositions which will "indicate" different minimum concentrations of glucose in solution. The proper proportion of antagonist compound required to obtain a reagent composition which will indicate the presence of a specific concentration of glucose in solution is readily calculated mathematically or may be determined by trial and error techniques, and is related to the amount of glucose reacting substantially in the usual stoichiometric manner.

The following examples describe the manner and process of making and using this invention and set forth the best mode contemplated by the inventor of carrying out the invention but are not to be construed as limiting. All parts are by weight unless otherwise indicated.

EXAMPLE I

A. To an appropriate vessel there is charged 300 micorliters of a solution of glucose oxidase (Sigma Chemical Company, St. Louis, Missouri, Catalog No. G-6500; glucose oxidase from molds having an activity of 1200 IU/ml.), 150 microliters of a solution of horseradish peroxidase [prepared by dissolving 37.5 milligrams of horseradish peroxidase (Sigma, supra, Catalog No. P-8250) in 1.0 milliliters of 0.01M citrate buffer (pH 5.5)], 300 microliters of 2,2′-azino-di-(3-ethyl-benzothiazoline-6-sulphonic acid) in solution [prepared by dissolving 50 milligrams of 2,2′-azino-di-(3-ethyl-benzothiazoline-6-sulphonic acid) (Boehringer Mannheim Corporation, New York, New York, product No. 15594) in 1.0 milliliters of 0.1M citrate buffer, pH 5.5], 50 microliters of 1% working solution of 2,5-DHBA (below), quantum sufficient to make a total of 1,250 microliters. The mixture is thoroughly admixed to obtain a glucose indicating reagent solution.

B. In an appropriate vessel 0.5 grams of 2,5-dihydroxybenzoic acid is slurried in 4 milliliters of water. To the slurry there is then added with stirring a solution of 10% sodium hydroxide in water until a clear solution is obtained. This is used as a stock 10% solution. A working 1% solution is prepared by appropriate dilution with 0.1M citrate buffer, pH 5.5

C. Four separate appropriate vessels are each charged with 75 microliters of the indicating reagent solution prepared in (A) above. In each vessel there is then added with mixing, various proportions of the 1% 2,5-dihydroxybenzoic acid solution prepared in (B), supra, and varying amounts of buffer as described in (A) above to obtain glucose indicating reagent solutions, each of which will indicate visually when exposed to various minimum concentrations of glucose in solution, by a color change of from substantially colorless to colored. The four vessels are identified by the letters A through D inclusive. The concentration of 2,5-dihydroxybenzoic acid and buffer in each vessel and the minimum glucose concentration of a solution which each reagent composition A through D inclusive will indicate by a color change are shown in Table 1 below.

TABLE I

| Vessel | Buffer (Microliters) | 2,5-DHBA (Microliters) | Concentration of 2,5-DHBA | Percent of Minimum Glucose Concentration in Solution Required for Indication to Occur |
| --- | --- | --- | --- | --- |
| A | 25 | 0 | 0.3% | 0.1% |
| B | 21 | 4 | 0.75% | 0.25% |
| C | 13 | 12 | 1.5% | 0.5% |
| D | 0 | 25 | 2.8% | 2.0% |

Similarly, following the procedure of Example I, part A above, but replacing the 2,5-DHBA as used therein with an equivalent proportion of indoxyl sulfate; Uric acid; 3,4-dihydroxymandelic acid; 3-methoxy-4-hydroxymandelic acid; 3,4-dihydroxyphenylacetic acid; 3-methoxy-4-hydroxyphenylacetic acid; 3,4-dihydroxyphenylalanine; 3-methoxy14-hydroxyphenylalanine; 5-hydroxyindole-3-acetic acid; 5-hydroxyindole-2-carboxylic acid; 5-hydroxytryptophane; creatinine; 2,5-dihydroxy- phenylacetic acid; o-hydroxytramine (dopamine); and 5-hydroxy-tryptamine, respectively, glucose indicating reagent solutions are obtained which are useful in fabricating indicator devices of the invention.

EXAMPLE II

A series of five sets of circular discs are prepared, each set consisting of four discs and each disc being fashioned from No. 52 Whatman filter paper by cutting out a circle, 4 mm, in diameter. Each disc within each set is then wetted with about 0.002 ml of a different one of the reagent solutions A, B, C and D, respectively, prepared in Example I, supra. The wet discs are allowed to air-dry. Each disc is calculated to contain, on drying, approximately 0.6 IU of glucose oxidase, 1.2 PU of peroxidase, 18 micrograms of citrate buffer, 24 micrograms of 2,2′-azine-di-(3-ethyl-benzothiazoline- 6-sulphonic acid) and varying proportions of 2,5-dihydroxybenzoic acid. The dry discs of each set are then mounted on a single paper strip, and each disc labeled a, b, c or d to correspond to the particular reagent A, B, C and D, respectively, employed in its preparation. Four of the paper strips each bearing a separate set of the four discs a–d is then immersed in one of four aqueous solutions containing 0.1 percent, 0.25 percent, 0.25 percent and 2.0 percent glucose respectively. The fifth strip is a control strip and is immersed in distilled water. Each strip is immersed in the solution for a period of about one second and then withdrawn. Within about 1 minute of immersion, each strip is observed for a change of color in the discs mounted thereon. The results are give in Table II below, with the proportion of 2,5-dihydroxybenzoic acid calculated to be present in each disc.

TABLE II

| Strip No. | % of Glucose in Immersion Solution | Disc | Proportion of 2,5-dihydroxybenzoic Acid (mcg) per disc | Color Change |
| --- | --- | --- | --- | --- |
| 1 | 0.1% | | | |
| | | a | 0.6 | Yes |
| | | b | 1.4 | No |
| | | c | 3.0 | No |
| | | d | 5.6 | No |
| 2 | 0.25% | | | |
| | | a | 0.6 | Yes |
| | | b | 1.4 | Yes |
| | | c | 3.0 | No |
| | | d | 5.6 | No |
| 3 | 0.5% | | | |
| | | a | 0.6 | Yes |
| | | b | 1.4 | Yes |
| | | c | 3.0 | Yes |
| | | d | 5.6 | No |
| 4 | 2.0% | | | |
| | | a | 0.6 | Yes |
| | | b | 1.4 | Yes |
| | | c | 3.0 | Yes |
| | | d | 5.6 | Yes |
| 5 (Control) | 0.0% | | | |
| | | a | 0.6 | No |
| | | b | 1.4 | No |
| | | c | 3.0 | No |
| | | d | 5.6 | No |

The color changes obtained were a distinct darkening, strongly positive, and those discs which did not change showed no appreciable darkening. The registrations obtained remained stable for at least 72 hours. This is not possible with the commercially available glucose indicators of the prior art which must be read, usually within minutes.

The indicator of the invention and the method of the invention will now be further illustrated by reference to the specific embodiments shown in the accompanying drawings.

In FIG. 1 there appears a perspective view of an indicator 20 of the invention. The indicator 20 comprises a support member which is shown in FIG. 1 as a flat strip 18 and which preferably is bibulous material such as an absorbent paper strip. Disposed on the strip 18 by impregnation thereon in a manner so as to form the numerals 1, 2, 3 and 4 are reagents 11, 12, 13 and 14 respectively. Reagent 11 is a composition such as composition A of Example I, supra. and will indicate by color change when a minimum glucose concentration of 0.1% is present in a solution brought into contact with the reagent. Reagents 12, 13 and 14 correspond to the reagent compositions B, C and D respectively of Example I, supra. and will indicate the minimum glucose concentrations of 0.25%, 0.5% and 2.0% in glucose containing solutions, respectively. The disposition of the reagent compositions on the support member 18 may of course be in any convenient indicia. For example, the minimum concentration indicated by a given reagent may be the form of disposition, i.e.; for example reagent 11 above described may be disposed in the configuration "0.1%". The numerals 1, 2, 3 and 4 selected for illustration in FIG. 1 is especially useful when the indicator device is to be employed for determining the glucose concentration of urine specimens. Such indicia conforms to the customary practice of referring to a 0.1% concentration of glucose in urine as a "plus 1" level, a 0.25% concentration as "plus 2", a 0.5% concentration as "plus 3" and a 2.0% concentration as "plus 4".

Prior to use, the symbols 1, 2, 3 and 4 employed in the embodiment of FIG. 1 may be invisible to view or only slightly decipherable through a slight discoloration upon strip 18. The broken lines indicating the numerals 3 and 4 are intended to show that the numerals 3 and 4 are not clearly decipherable as originally formed on member 18. Upon exposure however to a glucose solution by immersion therein, the reagents react chemically to produce a color. If the glucose concentration in the tested solution exceeds the minimum glucose concentration for which the reagent will give a color indication, such color change occurs. In the FIG. 1 numerals 1 and 2 are shown in distinct dark tones and illustrate the indication obtained following immersion of indicator 20 in a solution of glucose containing a glucose concentration of from between 0.25% and 0.55. Reagents 11 and 12 have reacted to indicate a "plus 2" concentration, i.e.; the highest number developed. The development of reagents 11 and 12 to produce a clear and distinct color change forming distinct solid numerals gives a direct reading to the user of the minimum glucose concentration in the solution tested. Thus, the method of the invention is carried out by immersing that portion of indicator 20 which bears reagents 11, 12, 13 and 14, into a glucose containing solution momentarily, withdrawing it and visually observing the indicia registered. It will be observed that the operator does not have to carry out a comparison of colors registered, with standard charts to determine the glucose concentration of the tested solution, as is necessary with prior art disposable devices. When the preferred composition of the invention is employed as the reagents 11, 12 13 and 14, clear and distinct indications of glucose concentration are obtained within about 1 minute. The indicia registered on the indicator are relatively stable and will last for a relatively long time so that at an interval of up to at least 72 hours after immersion and withdrawal of indicator 20, the user may refer back to recheck the test results. This is not possible with prior art devices.

The embodiment illustrated in FIG. 1 may obviously be modified in many respects to meet specific needs. The degree of sensitivity of each reagent may be modified to meet specific needs. Different ranges and sensitivities of the indicator devices may be obtained by selection of the reagent sensitivities and the number of different reagent compositions applied to the support member. Although the indicator shown in FIG. 1 is particularly well suited for testing urine for glucose content, appropriate selection of reagent compositions, range of indication and registrable indicia will yield indicators appropriately used for testing other biological fluids such as blood, sweat, urine and like biological liquids for glucose, albumin, ketone and other substances normally or abnormally found therein. The support member, strip 18 may also be dyed a particular color to either blend with the reagent compositions prior to their indicating the presence of glucose or they may be dyed a color to provide a very sharp contrast when the reagent reacts to produce a registration.

Figure 2:
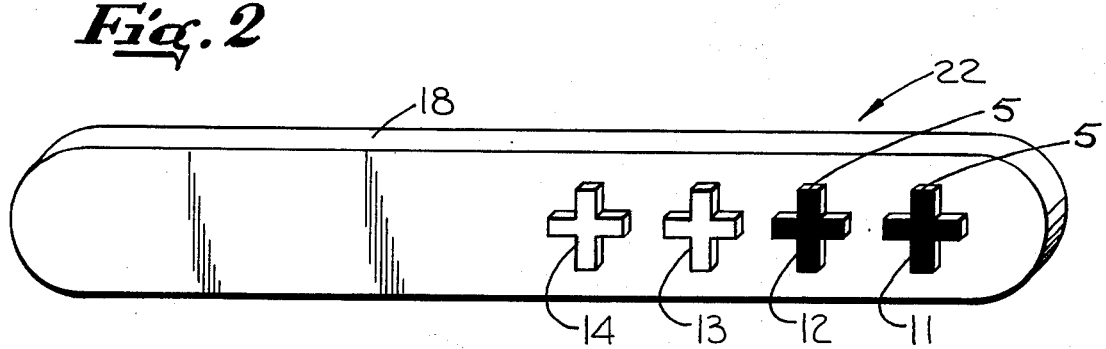
FIG. 2 is an isometric view of an alternate indicator embodiment of the invention after use.

As further examples of modifications which may be made to the basic indicator shown in FIG. 1, reference is made now to FIG. 2 which shows an isometric view of indicator 22 which may also comprise a support member 18 as described above and upon which there have been mounted "plus-shaped" blocks 5 of a bibulous material. Each block 5 has been saturated with a solution of a reagent 11, 12, 13 and 14 respectively as described above in conjunction with FIG. 1 and then dried before fixation upon support member 18. When indicator 22 is immersed briefly in a glucose containing solution the reagents carried on blocks 5 react as described above, and if the glucose level exceeds the minimum indicating sensitivity of the particular reagent, a color change in the block 5 carrying that reagent is visually observable. By counting the "pluses" which have changed color, the operator can read the device directly. In the device 22, as shown, a "plus-2" has been indicated, i.e.; the device was exposed to a solution containing between 0.25 and 0.5% glucose.

Figure 3:
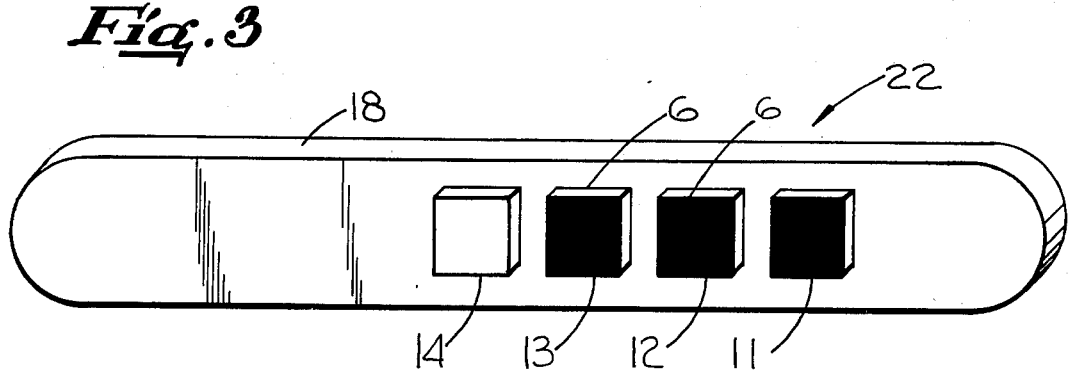
FIG. 3 is an isometric view of another embodiment of the invention after use.

FIG. 3 is an alternate embodiment similar to device 22 of FIG. 2, differing essentially in that the shape of the bibulous block 6 is a rectangle rather than a cross. This embodiment is operated in the same way as the device of FIG. 2 and as shown here has been exposed to a solution of glucose in the "plus-3" concentration range, i.e.; the solution tested had a glucose concentration of between 0.5% to 2%.

The embodiment of FIGS. 2 and 3 are particularly advantageous when the support member 18 is a hydrophobic material such as, for example, polyethylene. The blocks 5 and 6 will each then absorb a predetermined volume of the biological fluid being tested, upon immersion. When the indicator reagents 11, 12, 13 and 14 have been deposited on blocks 5 and 6 by saturation of said blocks 5 and 6 with the indicator reagents 11, 12, 13 and 14 in solution followed by evaporation of the reagent solvent, the volume of test solution absorbed in blocks 5 and 6 on immersion in test solution will be substantially equal to the volume of solvent evaporated from the blocks 5 and 6 to deposit the indicator reagent. This is the preferred ratio of volume of reagent in solution to volume of test solution absorbed as previously described, and results in a highly accurate, precise indicator device of the invention.

Those skilled in the art will appreciate that the fabrication of the preferred indicator devices of the invention according to the embodiments of FIGS. 2 and 3 discussed above may be relatively costly due to the requirements of preparing a bibulous carrier of specific dimensions, saturating the carrier with a specific volume of reagent solution containing a specific concentration of indicator reagent and drying the same on a supporting member. By a method of the invention, highly accurate and precise indicator devices of the invention such as those illustrated in FIGS. 2 and 3 may be prepared obviating a number of the requirements as outlined above, thereby reducing the cost of manufacture and providing improved indicator products.

The improved method of manufacture comprises slurrying or dissolving the bibulous material, with the indicator reagent, depositing the slurry or solution on a hydrophobic support member and evaporating the solvent to leave a residue of a dried mixture of indicator and bibulous material adhered to the support member. The slurry of bibulous material and indicator reagent in solvent may be prepared by admixture of the bibulous material in finely divided form with the reagent in solvent using conventional apparatus and technique. As an example, a slurry of cellulose powder or a solution of other bibulous material mixed with compositions of the invention dissolved in water may be prepared, deposited on a polyethylene stick and dried.

FIGS. 4a, 4b, 4c and 4d illustrate still another embodiment of the invention. The indicator device is referred to generally by the numeral 24 in these Figures. In FIG. 4a, indicator 24 is shown to comprise a support member 18 as described previously, but bearing reagents 11, 12, 13 and 14 as previously described in a sequence so that reagent 11 is disposed in the form of a symbol 1, reagent 12 is disposed in the form of a symbol 2 and is also disposed in a zone surrounding the symbol 1 formed by a reagent 11. In a similar manner ragent 13 is disposed in the form of a symbol 3 and also in the zone surrounding the symbol 2. Reagent 14 is disposed in the form of symbol 4 and also in the zone surrounding the symbol 3. In this embodiment, exposure to a glucose containing solution of a specific level will indicate numerically the minimum concentration of glucose in the tested solution and will obliterate numeral symbols for any lower concentrations of glucose. For example, FIG. 4a shows by broken lines the zones and disposition into indicia of the reagent compositions 12, 13 and 14 not registering the specific concentrations of glucose to which they are sensitive. The numeral 1 appears in bold outline as indicative of a "plus 1" concentration of glucose, meaning the indicator 24 as shown in FIG. 4a has been exposed to a solution containing at least 0.1% of glucose.

Referring to FIG. 4b, there is seen the registration obtained by immersion, briefly, of indicator device 24 in a test solution containing between 0.25% and 0.5% glucose concentration. The registration of the numeral 2 and obliteration of the also developed numeral 1. This is a clear indication to the user of a "plus 2" glucose concentration in the tested solution. FIG. 4c shows the indicia registered when indicator 24 was immersed in a solution containing between 0.5% and 2.0% glucose and FIG. 4d shows the indicia registered upon immersion of indicator 24 in a solution containing more than 2.0% glucose, i.e.; a "plus 4" reading.

Figure 5:
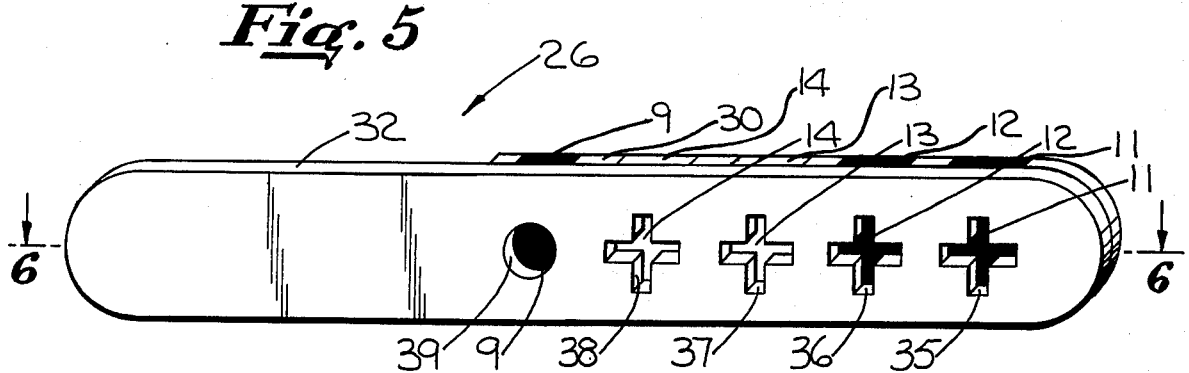
FIG. 5 is an isometric view of a preferred indicator embodiment of the invention shown after use in a glucose containing urine specimen.

FIG. 5 is an isometric view of a preferred indicator of the invention shown after use by immersion in a solution containing between 0.25% and 0.5% glucose. The preferred indicator 26 is particularly useful in urine analysis and comprises as a support member a bibulous material 30 which has been laminated to a strip 32 of stiff supporting material such as polymeric plastic for example a strip of polyethylene, polypropylene or like polymeric material. Apertures 35, 36, 37 and 38 have been cut into supporting strip 32 in the form of positive signs in those areas overlying support member 30 which have been impregnated with the various reagents 11, 12, 13 and 14 previously described. In this manner, the various zones of support member 30 bearing reagents 11, 12, 13 and 14 are viewed through the corresponding apertures 35, 36, 37 and 38 respectively. In addition, an area or zone of support member 30 has also been impregnated with a reagent 9 which is sensitive to an acid pH. The reagent 9 impregnated zone of support member 30 is visible through aperture 39 cut into strip 32. The purpose of the zone impregnated with reagent 9 is to serve as a control. When the indicator 26 is immersed in urine to determine glucose content thereof, contact of the urine with reagent 9 registers a color change. The user is then assured that all of the reagent zones below reagent 9 on member 30 have made contact with the urine solution, and therefore reagents 11, 12, 13 and 14 have been exposed to the urine specimen.

FIG. 6 is a cross-sectional view along lines 6—6 of FIG. 5 and shows in greater detail the mounting of support member 30 beneath the cutaway zones 35, 36, 37, 38 and 39 in rigid supporting strip 32. This embodiment, as illustrated in FIGS. 5 and 6, immediately provides the user, upon immersion in a urine specimen, with a visual indication of glucose level registered in terms of plus units which are readily calculated by counting the darkened indicia. Thus the illustrated device of FIGS. 5 and 6 has registered a "plus 2" value of glucose concentration, in the illustration.

Figure 7:
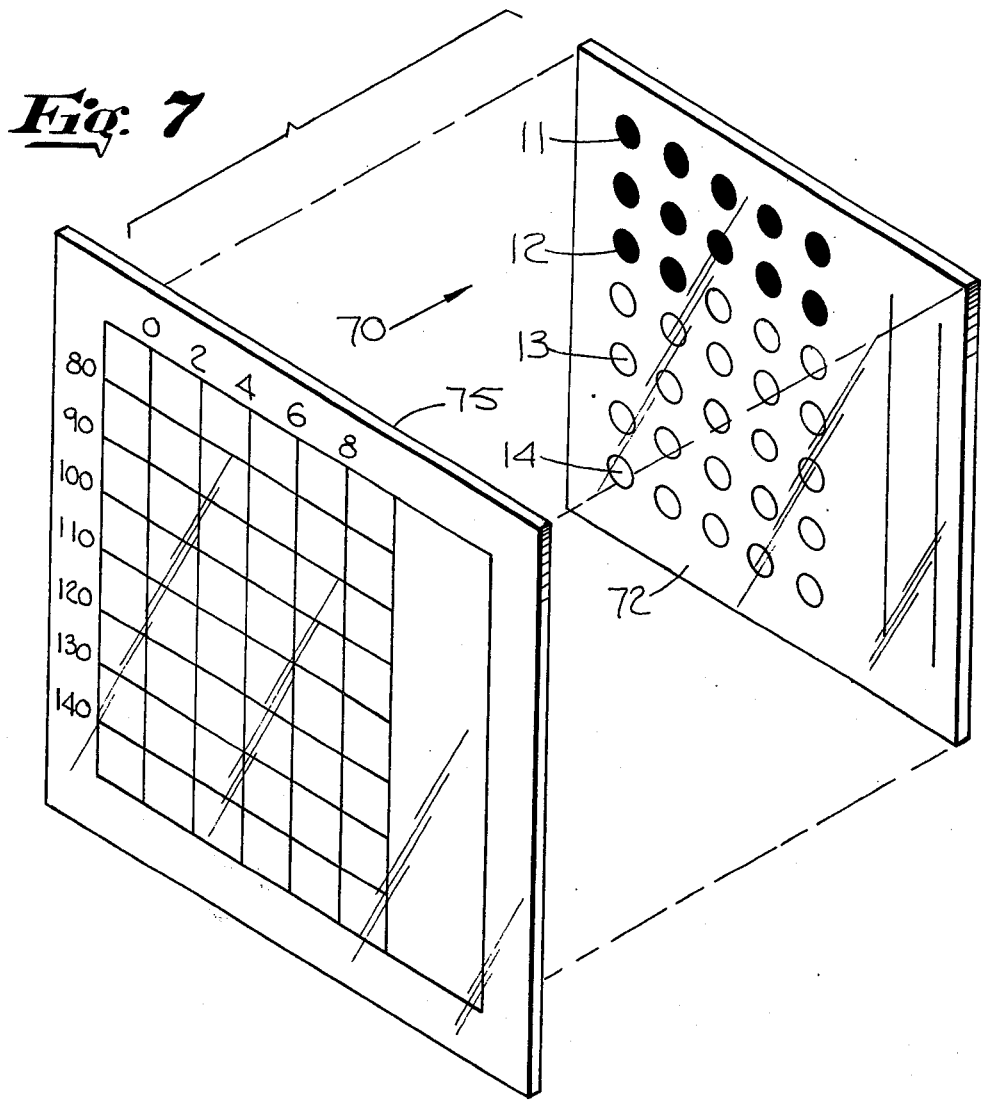
FIG. 7 is an isometric view of an alternate embodiment of the invention.

FIG. 7 is a view in perspective of another indicator embodiment of the invention which is particularly useful for precise determinations of the concentration of a substance dissolved in liquids, which potentially may have a broad range of possible concentrations. For example, the indicator shown generally by the numeral 70 is useful in measuring the glucose concentration of mammalian blood specimens. Indicator 70 comprises a transparent or highly translucent support member 72 such as a sheet of transparent cellulose acetate, a film of polyethylene, transparentized paper or like materials. Disposed on member 72 are a variety of reagents, such as reagents 11, 12, 13 and 14 previously described, with reagent compositions of intermediate sensitivities disposed between them as illustrated in the figure. Prior to exposure to a solution of glucose, for example blood serum, the zones covered by the various reagent compositions are relatively colorless. A sample of blood serum is wiped over the surface of the reagent bearing member 72, causing those reagents which indicate at the level of glucose concentration found in the blood specimen to undergo a visible color change. The indicator 70 is "read" by a hand held optical aid or by inserting it in a light projector with a reticule 75. Reticule 75 projects a reference grid, which is superimposed by projection over the indicator 70, whereby the indication registered on 70 is readily observed in a magnified and projected image. Of course when the indicator is to be read directly without the aid of a light projector, there is no need for a transparent support member 72.

The embodiment of the invention described above in relation to FIG. 7 is representative of another facet of the invention which comprises the use of reading aids, such as optical and electromechanical devices to assist in reading the indicators of the invention. More specifically the indicators of the invention function basically by the development of a color change, darkening or opacifying of a zone upon the support member component of the indicator device. Reading of the device is dependent upon an observation of a particular quantity of reacted or indicated zones. The actual "reading" of the indicators can therefore be performed mechanically by instruments designed to count symbols through the use of lenses, mirrors, filters, projectors, detectors and the like which can discriminate by means of light transmission, light reflectance, light scattering, electrical conductivity, radioactivity, etc. Thus, the reading of the indicator devices of the inventor may be carried out mechanically with the aid of photo scanners and like devices. This facet of the invention is particularly advantageous for use of the indicator devices of the invention bearing a large number of different reagent zones, each zone being of a microdot dimension or some dimension not readily observable with the naked eye. Such devices are particularly advantageous in that they use a minimum of reagent material, are fairly compact and can provide readings of great accuracy over wide ranges of possible substance concentrations in the solutions being tested.

The indicators of the invention may be used in ways not limited to those described in the foregoing. For example, before or after exposure to the test specimen, they may be exposed to reagents not previously incorporated in the reactive zones, or to a drying process, e.g. application of heat, or other chemical or physical agents selected for the purpose of developing or enhancing the appearance of visual or otherwise detectable indications.

What is claimed:

1. An indicator for the measurement of glucose dissolved in biological fluids, which comprises:
   a support member; and
   a plurality of indicating reagents for glucose, each of which is located in a separate zone of said member and at least two of which indicate the presence of different concentrations of glucose in solution.

2. The indicator of claim 1 wherein said support member is hydrophobic and said zones are formed of bibulous material.

3. The indicator of claim 1 wherein said reagents are disposed upon said support member in the shape of numerals corresponding to indicia for the level of glucose for which they indicate.

4. The indicator of claim 1 wherein said reagents are disposed upon said member in the order of their sensitivity.

5. The indicator of claim 1 wherein said reagents comprise an enzyme having glucose oxidase activity, peroxidase, an indicator which undergoes a color change in the presence of hydrogen peroxide and peroxidase and a compound which prevents the accumulation of oxidized indicator until such time as said compound has been completely consumed in such reaction.

6. The indicator of claim 1 wherein said support member is mounted on a stiffening member, said stiffening member having apertures therethrough for viewing said separate zones on the underlying support member, said apertures providing, by their shape, appropriate symbols of indicia.

7. The indicator of claim 6 wherein said stiffening member is a strip of polymeric material.

8. The indicator of claim 1 wherein there is also borne on said support member, a reagent which undergoes a color change in the presence of acid, the latter reagent being located in a separate zone of said support member.

9. The indicator of claim 1 wherein said support member is a transparent or translucent sheet.

10. The indicator of claim 1 wherein said indicating reagents comprise glucose oxidase, horseradish peroxidase, a compound which forms a color upon oxidation by hydrogen peroxide, a compound selected from the group consisting of indoxyl sulfate; Uric acid; 3,4-dihdroxylmandelic acid; 3-methoxy-4-hydroxymandelic acid; 3,4-dihydroxyphenylacetic acid; 3-methoxy-4-hydroxyphenylacetic acid; 3,4-dihydroxyphenylalanine; 3-methoxy-4-hydroxyphenylalanine; 5-hydroxyindole-3-acetic acid; 5-hydroxyindole-2-carboxylic acid; 5-hydroxytryptophane; creatinine; 2,5-dihydroxyphenylacetic acid; 0-hydroxytyramine (dopamine); 5-hydroxytryptamine; and 2,5-dihydroxybenzoic acid; and a buffer composition which will maintain the pH of said reagents within the range of from about 4 to about 6 in the presence of a biological fluid.

11. The indicator of claim 10 wherein the compound selected is 2,5-dihydroxybenzoic acid.

12. The indicator of claim 10 wherein the proportion of components of said reagents is:
40 IU or more of glucose oxidase;
60 PU or more of peroxidase;
from 0.05 to 15 mg. of said color forming compound; and
from 0.01 to 5 mg. of the selected compound, all in a final volume of about 100 microliters, 0.01 to 10 microliters of which is applied to each sensitive zone.

13. An assembly for the measurement of glucose dissolved in a biological fluid which comprises;
A. an indicator which comprises: a support member; and a plurality of indicating reagents for glucose each of which is disposed in a separate zone of said member and each of which upon exposure to a solution of said glucose will indicate visually if a different minimum concentration of glucose is present in said solution, by a darkening thereof; and
B. a reticule adapted to overlay said indicator and bearing thereon a reference grid corresponding to the order in which said reagents are disposed on said support member.

14. A method of determining the concentration of glucose in a biological solution which comprises:
immersing in said solution an indicator which comprises:
a support member; and
a plurality of indicating reagents for glucose, each of which is located in a separate zone of said member and at least two of which indicate the presence of a different concentration of glucose in solution by registering an indicia in said zone;
removing said indicator from said solution; and
reading the minimum concentration of glucose in said solution directly from the indicia registered.

15. A method according to claim 14 in which the concentration of glucose dissolved in said solution is determined by counting the number of indicia registered while reading.

16. A method according to claim 15 in which the registered indicia are counted in an electromechanical device.

17. A method according to claim 16 in which the zones are arranged in a linear manner and are counted by moving the indicator through the sensing zone of an electromechanical counter operated on the basis of detecting zones by their opacity, reflectance, radioactivity, fluorescence, luminescence, electrical conductivity, or other electromagnetic absorptive or radioactive property.

18. A glucose indicating composition which comprises:
glucose oxidase;
horseradish peroxidase;
a compound which forms a color upon oxidation by hydrogen peroxide;
a compound selected from the group consisting of indoxyl sulfate; Uric acid; 3,4-dihydroxymandelic acid; 3-methoxy-4-hydroxymandelic acid; 3,4-dihydroxyphenylacetic acid; 3-methoxy-4-hydroxyphenylacetic acid; 3,4-dihydroxyphenylalanine; 3-methoxy-4-hydroxyphenylalanine; 5-hydroxyindole-3-acetic acid; 5-hydroxyindole-2-carboxylic acid; 5-hydroxytryptophane; creatinine; 2,5-dihydroxyphenylacetic acid; o-hydroxytyramine (dopamine); 5-hydroxytryptamine; and 2,5-dihydroxybenzoic acid; and
a buffer composition which will maintain the pH of said glucose indicating composition within the range of from about 4 to about 6 in the presence of biological fluids.

19. A composition according to claim 18 wherein said selected compound is 2,5-dihydroxybenzoic acid.

20. A composition according to claim 18 -methoxy- the proportions of components is from 40 IU or more of glucose oxidase; 60 PU or more of peroxidase; 0.05 to 15 mg. of said color forming compound; and from 0.01 to 5.0 mg. of the compound selected from indoxyl sulfate; Uric acid; 3,4-dihydroxymandelic acid; 3-methoxy-4-hydroxymandelic acid; 3,4-dihydroxyphenylacetic acid; 3-methoxy-4-hydroxymandelic acid; 3,4-dihydroxyphenylacetic acid; 31methoxy-4-hydroxyphenylacetic acid; 3,4-dihydroxyphenylalanine; 3-methoxy-4-hydroxyphenylalanine; 5-hydroxyindole-3-acetic acid; 5-hydroxyindole-2-carboxylic acid; 5-hydroxytryptophane; creatinine; 2,5-dihydroxyphenylacetic acid; o-hydroxytyramine (dopamine); 5-hydroxytryptamine; and 2,5-dihydroxybenzoic acid; per 100 microliters of said buffer.

21. A composition according to claim 20 wherein said selected compound is 2,5-dihydroxybenzoic acid.

* * * * *

UNITED STATES PATENT OFFICE
CERTIFICATE OF CORRECTION

PATENT NO. : 3,964,871

DATED : June 22, 1976

INVENTOR(S) : Harry Hochstrasser

Page 1 of 2

It is certified that error appears in the above-identified patent and that said Letters Patent are hereby corrected as shown below:

At Column 7, line 25, - "frrom" should read -- from --

At Column 7, line 58, - "micorliters" should read -- microliters

At Column 8, line 48, - "methoxy 14-" should read -- methoxy -4- --

At Column 9, line 9, - "0.25" should read -- 0.5 --

At Column 10, line 32,- "0.55%" should read -- 0.5 --

At Column 12, line 25,- "ragent" should read -- reagent --

Col. 16, line 1, - "-methoxy-" should read -- wherein --

Col. 16, lines 8-16, inclusive, - "phenylacetic acid; 3-methoxy-4-hydroxymandelic acid; 3,4-dihydroxyphenylacetic acid; 31 methoxy-4-hydroxyphenylacetic acid; 3,4-dihydroxyphenylalanine; 3-methoxy-4-hydroxyphenylalanine; 5-hydroxyindole-3-acetic acid; 5-hydroxyindole-2-carboxylic acid; 5-hydroxytryptophane; creatinine; 2,5-dihydroxyphenylacetic acid; o-hydroxytyramine (dopamine); 5-hydroxytryptamine; and 2,5-dihydroxybenzoic acid; per 100 microliters of said buffer."

should read --

UNITED STATES PATENT OFFICE
CERTIFICATE OF CORRECTION

PATENT NO. : 3,964,871
DATED : June 22, 1976
INVENTOR(S) : Harry Hochstrasser

It is certified that error appears in the above-identified patent and that said Letters Patent are hereby corrected as shown below:

phenylacetic acid; 3-methoxy-4-hydroxyphenyl-acetic acid; 3,4-dihydroxyphenylalanine; 3-methoxy-4-hydroxyphenylalanine; 5-hydroxyindole-3-acetic acid; 5-hydroxyindole-2-carboxylic acid; 5-hydroxytryptophane; creatinine; 2,5-dihydroxyphenylacetic acid; o-hydroxytyramine (dopamine); 5-hydroxytryptamine; and 2,5-dihydroxybenzoic acid; per 100 microliters of said buffer. --

Signed and Sealed this

Twenty-seventh Day of September 1977

[SEAL]

Attest:

RUTH C. MASON
Attesting Officer

LUTRELLE F. PARKER
Acting Commissioner of Patents and Trademarks